US011774026B2

(12) United States Patent
Witherow

(10) Patent No.: US 11,774,026 B2
(45) Date of Patent: Oct. 3, 2023

(54) TUBE CONNECTION KIT

(71) Applicant: Randy Witherow, Baton Rouge, LA (US)

(72) Inventor: Randy Witherow, Baton Rouge, LA (US)

( * ) Notice: Subject to any disclaimer, the term of this patent is extended or adjusted under 35 U.S.C. 154(b) by 464 days.

(21) Appl. No.: 16/745,761

(22) Filed: Jan. 17, 2020

(65) Prior Publication Data

US 2020/0232590 A1    Jul. 23, 2020

Related U.S. Application Data

(60) Provisional application No. 62/794,752, filed on Jan. 21, 2019.

(51) Int. Cl.
*F16L 55/07*      (2006.01)
*A61M 1/00*      (2006.01)
*F16L 33/30*     (2006.01)

(52) U.S. Cl.
CPC ............. *F16L 55/07* (2013.01); *A61M 1/743* (2021.05); *F16L 33/30* (2013.01)

(58) Field of Classification Search
CPC ....... F16L 55/07; F16L 33/30; F16L 37/0841; A61M 1/743; A61M 39/10; A61M 2039/1016; A61M 39/24; A61M 2039/2413
USPC ....................................................... 604/284
See application file for complete search history.

(56) References Cited

U.S. PATENT DOCUMENTS

| | | | |
|---|---|---|---|
| 3,595,234 A | 7/1971 | Jackson | |
| 3,757,824 A | 9/1973 | Bungo et al. | |
| 5,273,533 A * | 12/1993 | Bonaldo | A61M 39/04 604/905 |
| 7,306,198 B2 | 12/2007 | Doyle | |
| 10,473,245 B2 * | 11/2019 | Ackermann | F16L 37/0841 |
| 10,794,525 B2 * | 10/2020 | Pennock | F16L 47/06 |
| 2005/0197647 A1 * | 9/2005 | Dolliver | A61M 39/24 604/541 |
| 2008/0265565 A1 | 10/2008 | Sitz et al. | |
| 2010/0147297 A1 | 6/2010 | Brewer et al. | |
| 2018/0345001 A1 * | 12/2018 | Heaton | A61M 1/912 |

* cited by examiner

*Primary Examiner* — Michael R Reid
(74) *Attorney, Agent, or Firm* — Boudwin Intellectual Property; Daniel Boudwin

(57) ABSTRACT

A tube connection kit for a vacuum system, and a method of clearing the vacuum system using the kit. The kit includes a female coupler and a male coupler. The male coupler includes a forward portion that connects to a first tube or a vacuum applicator, and a rearward portion that connects to a forward portion of the female coupler. A rearward portion of the female coupler connects to a second tube or a vacuum source. Interiors of the first tube or the vacuum applicator, the male coupler, the female coupler, and the second tube or the vacuum source are fluidly connected, such that a vacuum may be provided to the vacuum applicator. The female coupler includes a clearing valve that connects an exterior of the clearing valve to the interior of the female coupler, upon application of a fluid thereto, to allow clearing of the second tube.

7 Claims, 5 Drawing Sheets

TUBE CONNECTION KIT

CROSS REFERENCE TO RELATED APPLICATIONS

This application claims priority under 35 U.S.C. § 119(e) to U.S. Provisional Application No. 62/794,752 filed on Jan. 21, 2019. The above identified patent application is incorporated by reference herein in its entirety to provide continuity of disclosure.

BACKGROUND OF THE INVENTION

The present invention relates to a tube connection kit for connecting tubes of a vacuum system, and a method of using the kit to clear one or more tubes of the vacuum system.

Surgical procedures often require the use of a vacuum system for effective clearance of biological fluids and other materials from the operation site. This is important not only for the health of the patient, but also the health of the professionals performing the surgery, as exposure to these fluids can cause transmission of blood-borne pathogens from the patient to the professional. In addition, clearing the operation site ensures a clear field of vision for the surgeon, who needs to see internal organs and structures for surgical manipulation.

Existing tubing solutions for vacuum systems for medical procedures are unsatisfactory. They often break apart unexpectedly during use, resulting in spillage of biological fluids from the tube to the surrounding area. This spillage puts the medical professionals at risk of exposure to blood-borne pathogens, delays the surgical procedure, and endangers the patient. The breakage may occur as a result of rotation or twisting of a portion of the tubing with respect to another portion of the tubing, which results in torsional abnormalities that can break apart tubing connections or introduce kinks in the tubing which blocks the flow of fluid therein. In addition, biological fluids often comprise blood, which contains clotting factors. During the course of a procedure, biological fluid within the tube clots and forms blockages. Blockage results in the need to replace one or more tubes of the vacuum system, which is time-consuming and fraught with difficulty and additional risk of exposure to blood-borne pathogens.

Therefore, there is a need in the art for an improved tube connection kit for use with a vacuum system for a medical procedure, such as a surgery, and a method of clearing the vacuum system during use with the kit. The present invention addresses this unmet need.

Devices have been disclosed in the art that relate to surgical tubing. These include items that have been patented and published in patent application publications. These items are often incompatible with the dynamic nature of a surgical theater and result in frustration and unnecessary danger due to their structural and functional shortcomings. In view of the items disclosed in the art, it is submitted that there is a need in the art for an improvement to existing tubing connections for use with vacuum systems. In view of the present disclosure, it is submitted that the present invention substantially diverges in structural and functional elements from devices in the art, and substantially fulfills an unmet need in the art.

SUMMARY OF THE INVENTION

In view of the disadvantages inherent in the known types of vacuum tubing and tube connections in the art, the present invention provides a new and improved tube connection kit for a vacuum system, wherein the same can be utilized for maintaining tube connections through dynamic movements of the tubing, such as twisting and rotating, as may occur during surgical procedures. The kit can also be used for efficiently clearing blockages from one or more sections of the tubing of the vacuum system, without the need to disassemble the tubing.

It is therefore an object of the present invention to provide a tube connection kit for a vacuum system, and a method of clearing the vacuum system using the kit.

In one aspect, the invention provides a tube connection kit for a vacuum system, comprising a female coupler and a male coupler. The female coupler and the male coupler each comprises a forward portion with a forward aperture thereon and a rearward portion with a rearward aperture thereon. The female coupler further comprises a clearing valve that conditionally and fluidly connects an exterior of the clearing valve to an interior of the female coupler. During assembly of the kit with the vacuum system, the forward portion of the male coupler connects to a first tube or a vacuum applicator, the rearward portion of the male coupler connects to the forward portion of the female coupler, and the rearward portion of the female coupler connects to a second tube or a vacuum source. A vacuum, e.g., from the vacuum source, is provided to the first tube or the vacuum applicator to remove a substance from an area, such as a biological fluid from an operation site.

In some embodiments, the clearing valve is a one-way valve biased toward a closed configuration. In such embodiments, a bias of the one-way valve is overcome by application of a fluid against the one-way valve, whereby the one-way valve is placed into an open configuration. Because the one-way valve is biased toward the closed configuration, it does not open when not needed, and fluids are kept within the tubing. In this manner, the clearing valve only opens when forced open, such as by the application of the fluid, e.g., saline, thereto to clear the tubing of obstructions. Opening the clearing valve fluidly connects the interior of the female coupler and any connected tubing to the exterior of the clearing valve for clearing the female coupler and the tubing of obstructions.

In various embodiments, the clearing valve extends from the female coupler in a forward direction, at an angle, such that the angle between the clearing valve and the female coupler is less than ninety degrees. In some embodiments, the angle is about forty five degrees. In this manner, application of fluid to the clearing valve occurs such that the fluid readily travels with the direction of the vacuum, i.e., toward the vacuum source, after passing through the clearing valve to clear the system of obstructions.

In various embodiments, mushroom heads may be utilized for portions of the male and female couplers to facilitate insertion into another structure during assembly of the kit. For example, in such embodiments, the rearward portion of the female coupler comprises a mushroom head with the rearward aperture of the female coupler on a central portion thereof, such that the mushroom head of the rearward portion of the female coupler slips into the second tube or the vacuum source. In some such embodiments, the forward and rearward portions of the male coupler each comprises a mushroom head with the forward and rearward apertures on central portions thereof respectively. In this manner, the mushroom head of the forward portion of the male coupler slips into the first tube or the vacuum applicator, and the mushroom head of the rearward portion of the male coupler slips into the forward portion of the female coupler.

A feature of the present invention is the ability of the kit to be quickly and easily assembled and disassembled. This is accomplished, in part, through the use of a release button for disengaging the connection between the male and female couplers. Accordingly, in certain embodiments, the forward portion of the female coupler comprises a release button slidably engaged therewith, such that if the release button is in an extended configuration the forward aperture is unobstructed, and if the release button is in a retracted configuration the forward aperture is at least partially obstructed. When the kit is assembled and the release button is depressed, a portion of the release button displaces the rearward portion of the male coupler from the forward portion of the female coupler and the connection is disrupted. In some embodiments, after displacing the male coupler and disrupting the connection, the portion of the release button slips through a release slit positioned opposite the release button that slidably accepts the release button therethrough in the retracted configuration.

In another aspect, the invention provides a method of clearing a vacuum system, comprising connecting a forward portion of a male coupler to a first tube or a vacuum applicator, connecting a rearward portion of the male coupler to a forward portion of a female coupler, connecting a rearward portion of the female coupler to a second tube or a vacuum source, and applying a fluid to a clearing valve of the female coupler to place the clearing valve into an open configuration such that an exterior of the clearing valve is fluidly connected to an interior of the female coupler. The vacuum pulls the fluid through the interior of the female coupler and the second tube or the vacuum source to clean the second tube or the vacuum source.

In some embodiments of the method, a syringe is utilized to apply the fluid to the clearing valve. The clearing valve may be a one-way valve biased toward a closed configuration. After depressing a plunger of the syringe, the fluid is delivered from a barrel of the syringe to the one-way valve to overcome a bias of the one-way valve to place the one-way valve into the open configuration for cleaning the system with the fluid, e.g., saline.

Another object of the present invention is to provide a tube connection kit that may be readily manufactured from materials that permit relative economy and are commensurate with durability.

Other objects, features and advantages of the present invention will become apparent from the following detailed description taken in conjunction with the accompanying drawings.

BRIEF DESCRIPTIONS OF THE DRAWINGS

Although the characteristic features of the invention will be particularly pointed out in the claims, the invention itself and manners in which it may be made and used may be better understood after a review of the following description, taken in connection with the accompanying drawings, wherein like numeral annotations are provided throughout.

DETAILED DESCRIPTION OF THE INVENTION

Figure 1A:
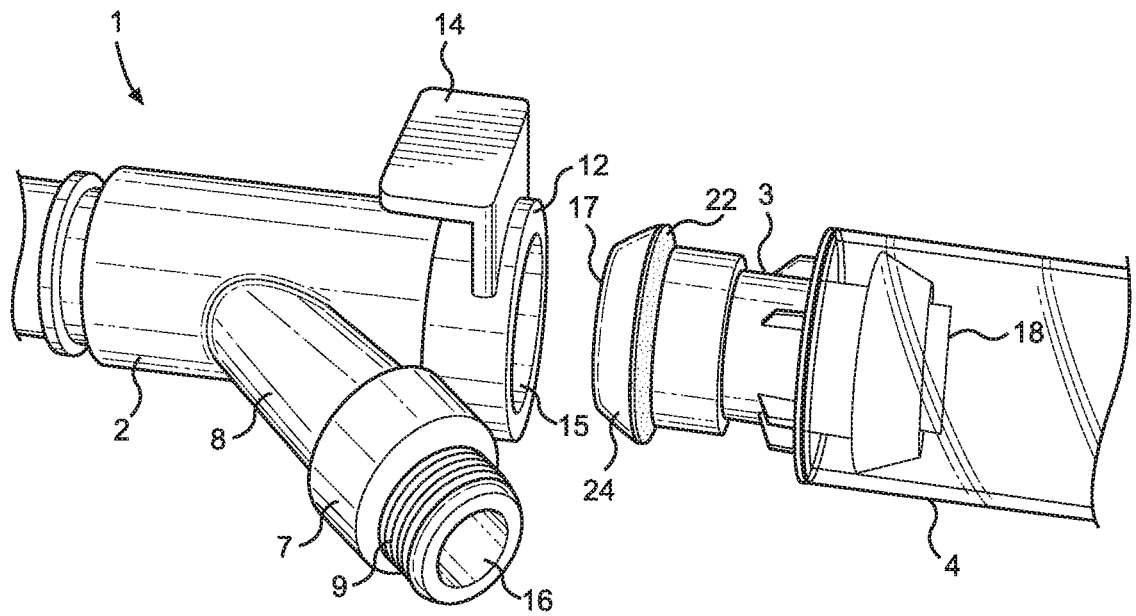
FIG. 1A depicts a perspective view of a tube connection kit for a vacuum system, in a disconnected state.

Reference is made herein to the attached drawings. Like reference numerals are used throughout the drawings to depict like or similar elements of the invention. The figures are intended for representative purposes only and should not be considered limiting in any respect.

Figure 1B:
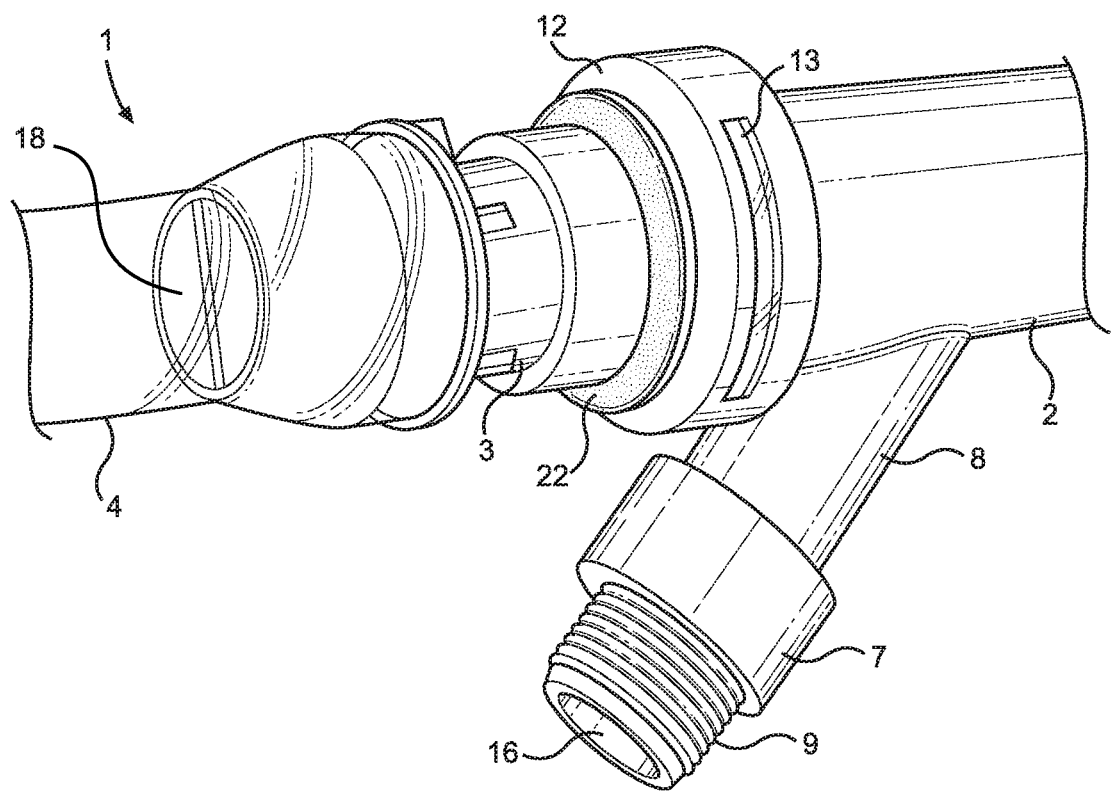
FIG. 1B depicts a perspective view of the tube connection kit, in a connected state.

Retelling now to FIGS. 1A and 1B, there are depicted perspective views of a tube connection kit for a vacuum system, in a disconnected (FIG. 1A) and in a connected (FIG. 1B) state. A true connection kit 1 includes a female coupler 2 and a male coupler 3. The female coupler 2 comprises a forward portion 12, and the male coupler 3 comprises a forward portion 18. The forward portions (12, 18) of the female coupler 2 and the male coupler 3 each includes a forward aperture thereon. In addition, the female coupler 2 comprises a rearward portion, and the male coupler 3 includes a rearward portion 17. The rearward portions of the female coupler 2 and the male coupler 3 each includes a rearward aperture thereon. In this manner, when the couplers (2, 3) are connected, interiors of the male coupler 3 and the female coupler 2 are fluidly connected.

The female coupler 2 further comprises a clearing valve 8 thereon at conditionally and fluidly connects an exterior of the clearing valve 8 to an interior of the female coupler 2, as explained elsewhere herein. In addition, during assembly of the kit 1 with the vacuum system, the forward portion 18 of the male coupler 3 connects to a first tube 4 or a vacuum applicator, the rearward portion 17 of the male coupler 3 connects to the forward portion 12 of the female coupler 2, and the rearward portion of the female coupler 2 connects to a second tube or a vacuum source. When a vacuum is supplied from the vacuum source, either directly to the second tube or indirectly through a fluid connection via a plurality of tubes, the vacuum is provided to the first tube 4 or the vacuum applicator via the fluid connection through the components of the kit, as would be understood by a person having ordinary skill in the art. After the vacuum is provided to the first tube 4 or the vacuum applicator, an operator is able to remove a substance from an area, such as a biological fluid from an operation site.

The clearing valve 8 includes an annular ridge 7 thereabout, which serves as a stricture against which a fluid delivery tool, such as a syringe, rests when the fluid delivery tool is connected to the clearing valve 8 for delivery of a fluid to the clearing valve 8. The clearing valve 8 includes an aperture 16 on a distal end thereof for accepting the fluid delivery tool therein, and delivery of the fluid therethrough. In this manner, the system and any tubing connected thereto may be easily cleaned or flushed for removal of blockages or debris. In the shown embodiment, the annular ridge 7 includes a threading 9 thereon, for secure and reversible attachment to the fluid delivery tool during use.

In various embodiments, the clearing valve 8 is a one-way valve biased toward a closed configuration. In such embodiments, a bias of the one-way valve is overcome by application of the fluid against the one-way valve, e.g., via the syringe, to place the one-way valve into an open configuration. Because the one-way valve is biased toward the closed configuration, it does not open when not needed, and fluids are kept within the tubing; in this manner, the clearing valve 8 only opens when forced open, such as by the application of the fluid, e.g., saline, thereto to clear the tubing of obstructions. Opening the clearing valve 8 fluidly connects the interior of the female coupler 2 and any connected tubing to the exterior of the clearing valve 8 for clearing female coupler 2 and the tubing of obstructions.

In various embodiments, such as the shown embodiment, the clearing valve 8 extends from the female coupler 2 in a forward direction (i.e., toward the forward portion 12 of the female coupler 2), at an angle, such that the angle between the clearing valve 8 and the female coupler 2 is less than ninety degrees. In the shown embodiment, the angle is about forty five (45) degrees. In this manner, applying the fluid to the clearing valve 8 occurs such that the fluid readily travels with the direction of the vacuum.

Mushroom heads may be utilized for portions of the male (3) and female (2) couplers, to facilitate insertion into another structure during assembly of the kit. For example, in such embodiments, the rearward portion of the female coupler 2 comprises a mushroom head with the rearward aperture of the female coupler 2 on a central portion thereof. In some such embodiments, the forward 18 and rearward 17 portions of the male coupler 3 each comprises a mushroom head with the forward and rearward apertures on central portions thereof respectively. In this manner, the mushroom head of the forward portion 18 of the male coupler 3 slips into the first tube 4 or the vacuum applicator, and a mushroom head 24 of the rearward portion 17 of the male coupler 3 slips into an aperture 15 of the forward portion 12 of the female coupler 2.

In various embodiments, the mushroom head 24 of the rearward portion 17 of the male coupler 3 is sized to snugly fit into the aperture 15 of the forward portion 12 of the female coupler 2. A feature of the present invention is the ability of the kit 1 to be quickly and easily assembled and disassembled. This is accomplished, in part, through the use of a release button 14 for disengaging the connection between the mushroom head 24 and the aperture 15. In certain embodiments, the forward portion 12 of the female coupler 2 comprises the release button 14 slidably engaged therewith, such that if the release button 14 is in an extended configuration (as shown in FIG. 1A), the forward aperture 15 is unobstructed, and if the release button is in a retracted configuration (as it would be if it were depressed by the operator), the forward aperture 15 is at least partially obstructed. When the kit 1 is assembled (as shown in FIG. 1B) and the release button 14 is depressed, a portion of the release button 14 displaces the mushroom head 24 from the forward aperture 15 and the connection between the male (3) and female (2) couplers is disrupted. In the shown embodiment, after displacing the male coupler 3 and disrupting the connection, the portion of the release button 14 slips through a release slit 13 positioned opposite the release button 14 that slidably accepts the release button 14 therethrough in the retracted configuration.

In various embodiments, an O-ring 22 is annularly affixed to the male coupler 3 and is configured to seal the connection between the female coupler 2 and the male coupler 3 during assembly and use of the kit 1 of the invention. With the inclusion of the O-ring 22, leakage from the coupled components (2, 3) is minimized and/or prevented, and fluids are kept within the male (3) and female (2) couplers.

In some embodiments, a first portion of the male coupler 3 freely rotates with respect to a second portion of the male coupler 3. In such embodiments, the male coupler 3 relieves torsional strain that may come about as a result of rotating a portion of the vacuum system, such as tubing or the vacuum applicator, as would be understood by a person having ordinary skill in the art. Because the torsional strain is relieved, blockage or disruption of vacuum delivery from the vacuum source to the vacuum applicator is prevented, and the system may be used continuously, even in a busy or dynamic surgical theater.

Figure 2:
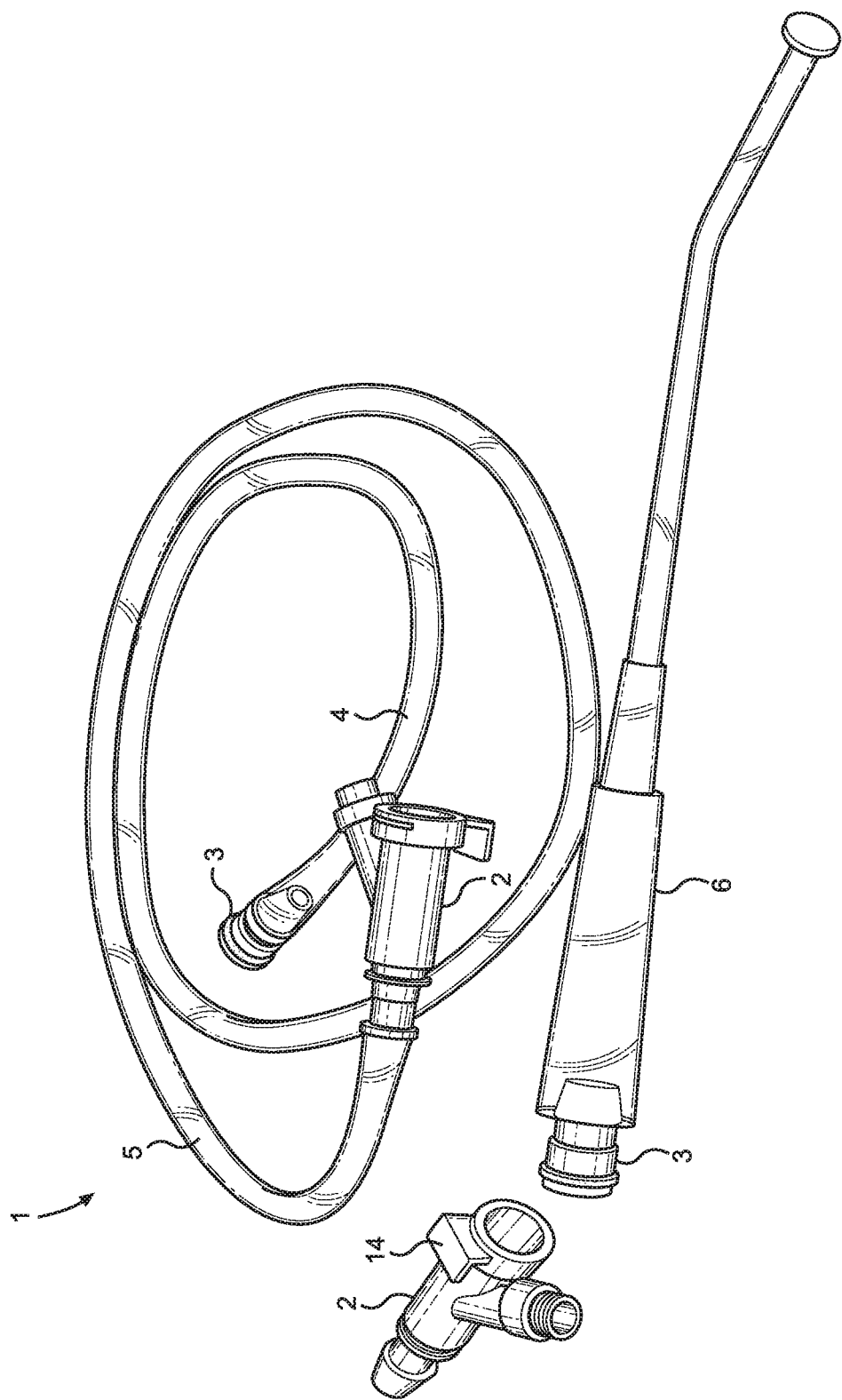
FIG. 2 depicts a perspective view of the tube connection kit, a tube, and a vacuum applicator.

Referring now to FIG. 2, there is depicted a perspective view of the tube connection kit, a tube, and a vacuum applicator. In the shown embodiment, the kit 1 includes the female coupler 2 with the release button 14 thereon, and the male coupler 3. A plurality of couplers (2, 3) may be included and attached in tandem for an extended line of tubing. In the shown embodiments, the tubing includes the first tube 4 connected to the male coupler 3, and the second tube 5 connected to the female coupler 2. In the shown embodiment, the first tube 4 and the second tube 5 comprise a single tube.

Any of a variety of different vacuum applicators 6 may be utilized with the kit 1 of the present invention, and in this manner, the kit 1 is highly modular. It is contemplated that the forward portion of the male coupler 3 be inserted into a base portion of the vacuum applicator 6, and the rearward portion of the male coupler 3 inserted into the forward portion of the female coupler 2, as described elsewhere herein. Thus, depending on what is attached to the male coupler 3 and the female coupler 2, the release button 14 can be utilized to quickly switch the vacuum applicator 6, remove the kit 1 from the vacuum source, remove or replace sections of tubing, and the like.

Figure 3:
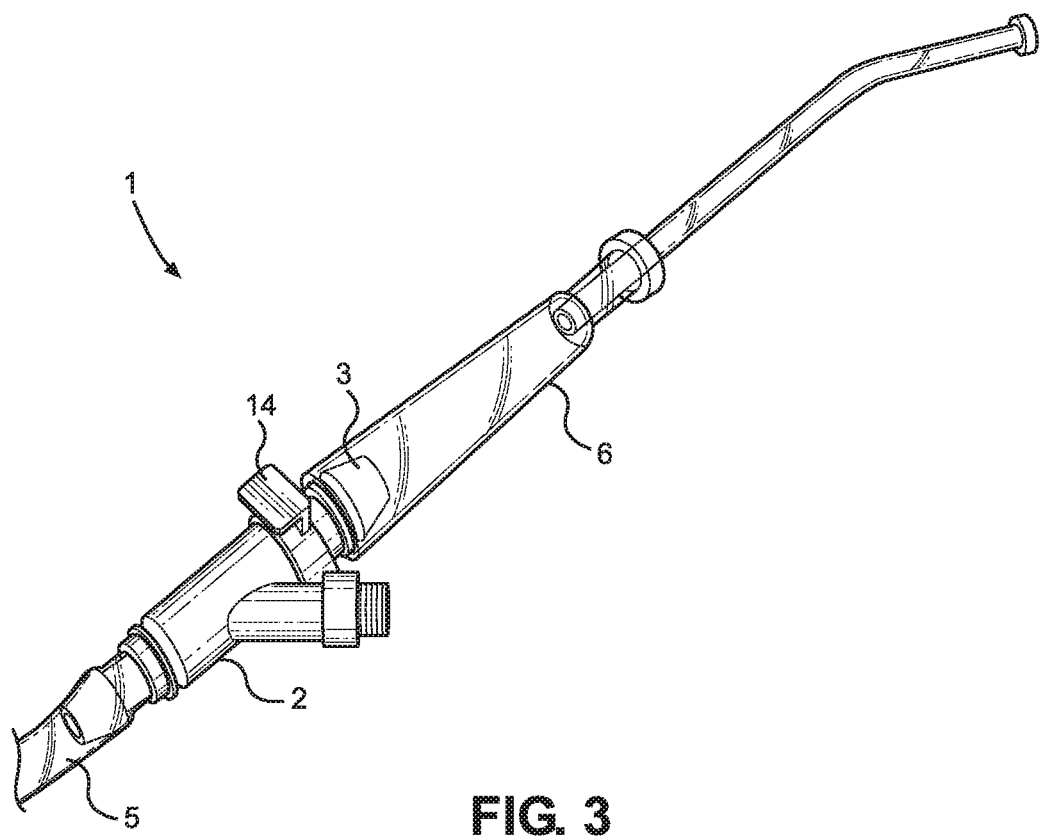
FIG. 3 depicts a perspective view of the tube connection kit, with the tube and the vacuum applicator connected thereto.

Referring now to FIG. 3, there is depicted a perspective view of the tube connection kit, with the tube and the vacuum applicator connected thereto. The kit 1 is depicted as being utilized to connect the vacuum applicator 6 to the tube 5 via a connection between the male coupler 3 and the female coupler 2. In the shown embodiment, depression of the release button 14 would cause the male coupler 3 to become detached from the female coupler 2, and the vacuum applicator 6 may be quickly removed from the tube 5.

Figure 4:
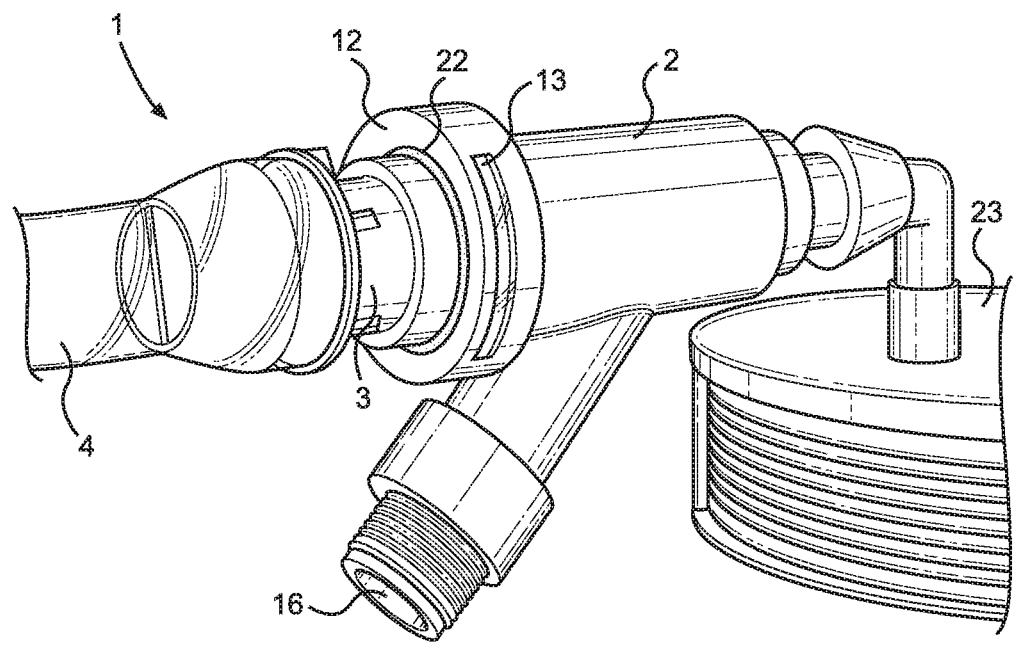
FIG. 4 depicts a perspective view of the tube connection kit, with a female coupler connected to a vacuum source.

Referring now to FIG. 4, there is depicted a perspective view of the tube connection kit, with a female coupler connected to a vacuum source. In the shown embodiment, the kit 1 is used to connect the tube 4 to a vacuum source 23. The male coupler 3 is connected to the female coupler 2, and the forward portion 12 of the female coupler 2 is shown as snugly engaging the O-ring 22 of the male coupler 3 to form a seal. In the shown embodiment, depression of the release button would cause the male coupler 3 to become detached from the female coupler 2, and the vacuum source 23 may be quickly removed from the tube 4. After depression of the release button, a portion of the release button may extend through the release slit 13.

Figure 5:
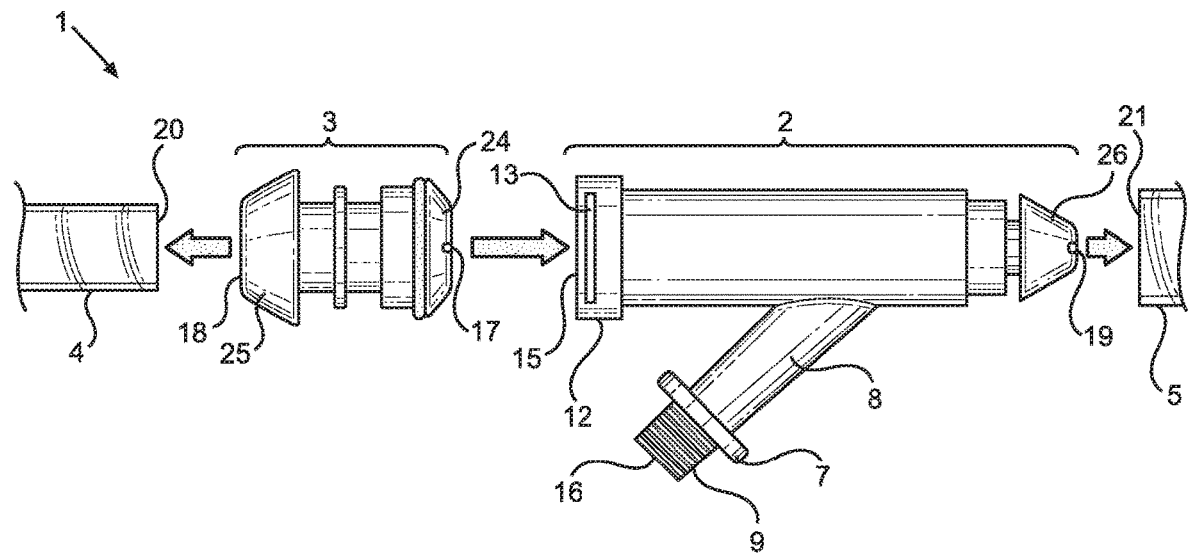
FIG. 5 depicts a side view of the tube connection kit, in a disassembled and disconnected state.
Figure 6:
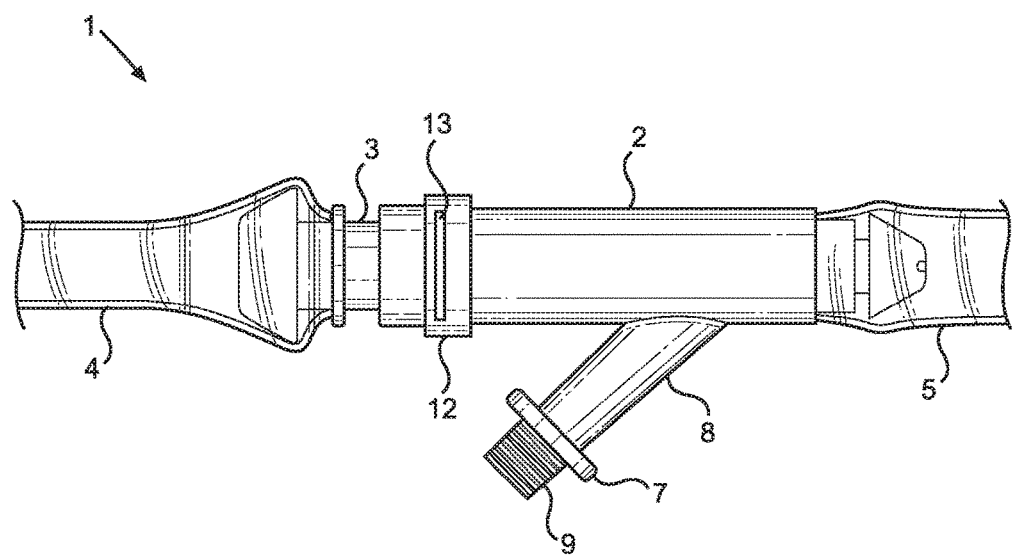
FIG. 6 depicts a side view of the tube connection kit, in an assembled and connected state.
Figure 7:
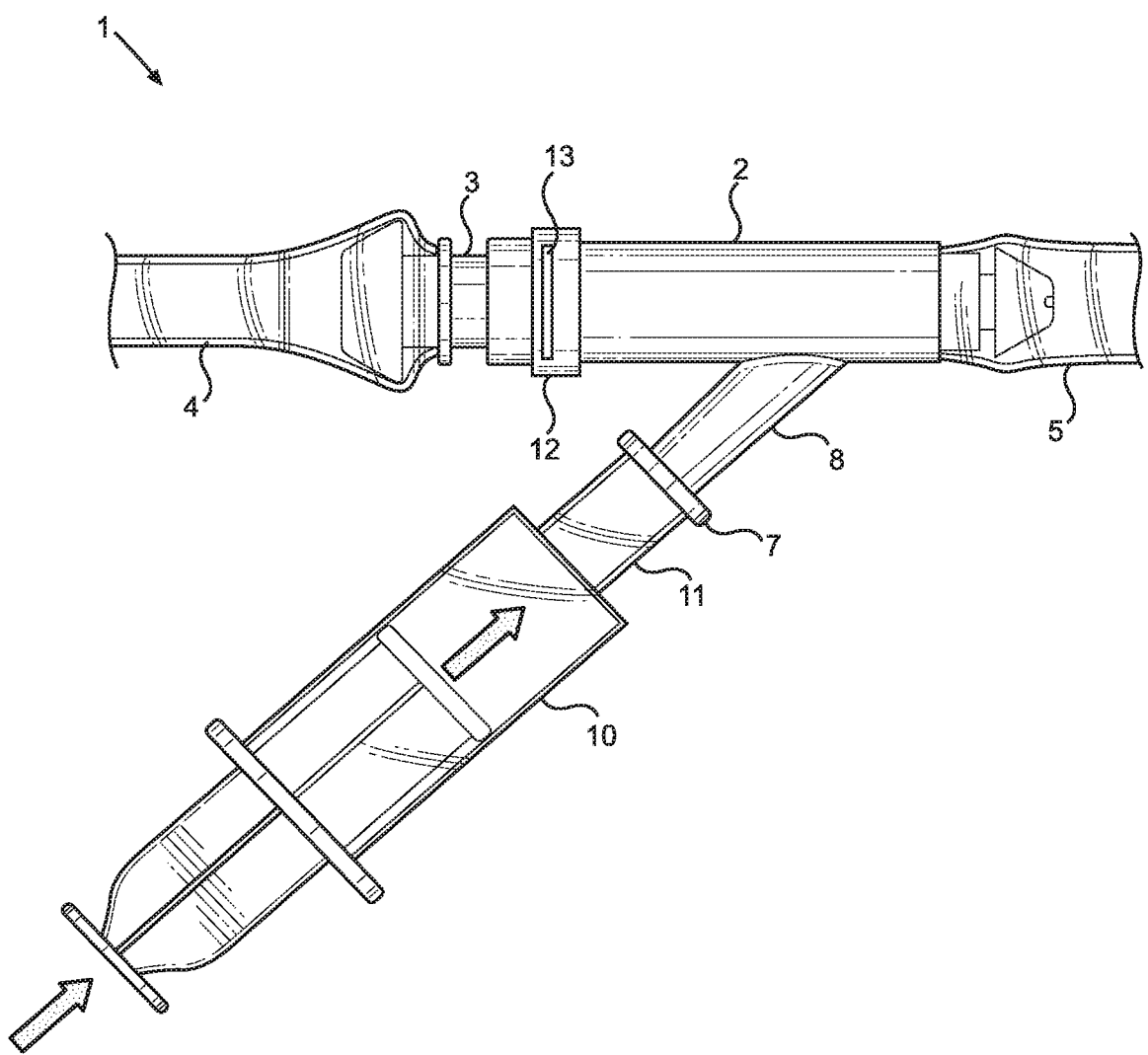
FIG. 7 depicts a side view of the tube connection kit, in the assembled and connected state, with a syringe connected to a clearing valve for cleaning the system.

Referring now to FIGS. 5-7, there are depicted a side view of the tube connection kit, in a disassembled and disconnected state (FIG. 5), in an assembled and connected state (FIG. 6), and in the assembled and connected state, with a syringe connected to a clearing valve for cleaning the system (FIG. 7). The kit 1 is shown as part of a method of clearing the vacuum system. The method comprises connecting the forward portion 18 of the male coupler 3 to the first tube 4

(or the vacuum applicator, according to a particular embodiment), connecting the rearward portion 17 of the male coupler 3 to the forward portion 12 of the female coupler 2 (with the aperture 15 thereon), connecting a rearward portion 26 of the female coupler 2 (with an aperture 19 thereon) to the second tube 5 (or the vacuum source, according to a particular embodiment), and applying the fluid to the clearing valve 8 of the female coupler 2 to place the clearing valve 8 into the open configuration such that e exterior of the clearing valve 8 is fluidly connected to the interior of the female coupler 2. The vacuum pulls the fluid through the interior of the female coupler 2 and the second tube 5 (or the vacuum source) to clean the second tube 5 (or the vacuum source).

The couplers (2, 3) of the kit 1 are used to fluidly connect the first tube 4 to the second tube 5, to connect the vacuum applicator to the second tube 5, and/or to connect the first tube 4 to the vacuum source. As would be understood by a person having ordinary skill in the art, any number of sections of tubing may be linked together by the couplers (2, 3) of the kit 1 of the present invention, with a particular use being delivery of a vacuum from the vacuum source to the vacuum applicator for removal of substances from an area.

In the shown embodiment, the first tube 4 includes an aperture 20 thereon, which is expandable to fit around the forward portion 18 of the male coupler 3 (with the mushroom head 25 thereon). The rearward portion 17 of the male coupler 3 (with the mushroom head 24 thereon) fits snugly into the aperture 15 of the rearward portion 12 of the female coupler 2, and this interaction is able to be disrupted by depressing the release button, which may slip through the release slit 13 of the rearward portion 12 of the female coupler 2. The female coupler 2 includes the clearing valve 8 thereon, extending therefrom in the angled forward direction, and the clearing valve 8 includes the annular ridge 7 with the threading 9 thereon, and the aperture 16 also thereon. The rearward portion 26 of the female coupler 2 includes the aperture 19 thereon and includes a mushroom head shape which fits into an aperture 21 of the second tube 5 (or the vacuum source). After attaching the couplers (2, 3) together and to the tubing as depicted in FIG. 6, a syringe 10, such as a Luer-Lok™ syringe, may be connected to the clearing valve 8 for cleaning of the vacuum system or portions thereof. Such a connection may be facilitated by a threaded portion 11 of the syringe, which reversibly engages the threading 9 of the clearing valve 8.

As such, in certain embodiments of the method, the syringe 10 is utilized to apply the fluid to the clearing valve 8. The clearing valve 8 may be a one-way valve biased toward the closed configuration. After depressing a plunger of the syringe 10, the fluid is delivered from a barrel of the syringe 10 to the one-way valve to overcome a bias of the one-way valve to place the one-way valve into the open configuration for cleaning the system with the fluid, e.g., saline.

The foregoing descriptions of specific embodiments of the present invention have been presented for purposes of illustration and description. They are not intended to be exhaustive or to limit the present invention to the precise forms disclosed, and modifications and variations are possible in view of the above teaching. The exemplary embodiment was chosen and described to best explain the principles of the present invention and its practical application, to thereby enable others skilled in the art to best utilize the present invention and its embodiments with modifications as suited to the use contemplated.

It is therefore submitted that the present invention has been shown and described in the most practical and exemplary embodiments. It should be recognized that departures may be made which fall within the scope of the invention. With respect to the description provided herein, it is submitted that the optimal features of the invention include variations in size, materials, shape, form, function and manner of operation, assembly, and use. All structures, functions, and relationships equivalent or essentially equivalent to those disclosed are intended to be encompassed by the present invention.

The invention claimed is:

1. A tube connection kit for a vacuum system, comprising:
a female coupler and a male coupler, wherein the female coupler and the male coupler each comprises a forward portion with a forward aperture thereon and a rearward portion with a rearward aperture thereon;
wherein the female coupler further comprises a clearing valve that conditionally and fluidly connects an exterior of the clearing valve to an interior of the female coupler;
wherein the forward portion of the male coupler connects to a first tube or a vacuum applicator, wherein the rearward portion of the male coupler connects to the forward portion of the female coupler, wherein the rearward portion of the female coupler connects to a second tube or a vacuum source;
wherein a vacuum is provided to the first tube or the vacuum applicator;
wherein the forward portion of the female coupler comprises a release button slidably engaged therewith, wherein when the release button is in an extended configuration the forward aperture is unobstructed, wherein when the release button is in a retracted configuration the forward aperture is at least partially obstructed;
wherein the forward portion of the female coupler comprises a release slit positioned opposite the release button that slidably accepts the release button therethrough in the retracted configuration; and
wherein in the extended configuration a connection between the male coupler and the female coupler is maintained, wherein in the retracted configuration the connection between the male coupler and the female coupler is disrupted and the male coupler is decoupled from the female coupler.

2. The tube connection kit of claim 1, wherein the clearing valve is a one-way valve biased toward a closed configuration, wherein a bias of the one-way valve is overcome by application of a fluid against the one-way valve, whereby the one-way valve is placed into an open configuration.

3. The tube connection kit of claim 2, wherein in the open configuration, the exterior of the clearing valve is fluidly connected to the interior of the female coupler.

4. The tube connection kit of claim 1, wherein the clearing valve extends from the female coupler in a forward direction, wherein an angle between the clearing valve and the female coupler is less than ninety degrees.

5. The tube connection kit of claim 4, wherein the angle is forty-five degrees.

6. The tube connection kit of claim 1, wherein the rearward portion of the female coupler comprises a mushroom head with the rearward aperture of the female coupler on a central portion thereof, wherein the mushroom head of the rearward portion of the female coupler slips into the second tube or the vacuum source.

7. The tube connection kit of claim 6, wherein the forward and rearward portions of the male coupler each comprises a mushroom head with the forward and rearward apertures on central portions thereof respectively, wherein the mushroom head of the forward portion of the male coupler slips into the first tube or the vacuum applicator, wherein the mushroom head of the rearward portion of the male coupler slips into the forward portion of the female coupler.

* * * * *